United States Patent [19]

Suoranta

[11] Patent Number: 5,427,943
[45] Date of Patent: Jun. 27, 1995

[54] HIGH DENSITY YEAST PREPARATION, A METHOD FOR PRODUCING IT AND THE USE OF THE PREPARATION

[75] Inventor: Kari Suoranta, Espoo, Finland

[73] Assignee: Alko Ltd., The Finnish State Alcohol Company, Helsinki, Finland

[21] Appl. No.: 86,467

[22] Filed: Jul. 6, 1993

Related U.S. Application Data

[63] Continuation of Ser. No. 655,816, Feb. 15, 1991, abandoned.

[30] Foreign Application Priority Data

Feb. 16, 1990 [FI] Finland ................................ 900804

[51] Int. Cl.$^6$ ............................ C12N 1/16; A21D 8/04
[52] U.S. Cl. ................................. 435/255.1; 426/62
[58] Field of Search ............... 435/255.1, 260; 426/62

[56] References Cited

U.S. PATENT DOCUMENTS

| Re. 28,276 | 12/1974 | Farr | 195/96 |
|---|---|---|---|
| 3,960,664 | 6/1976 | Olsen et al. | 435/252.9 |
| 4,160,040 | 7/1979 | Luca et al. | 435/256 |
| 4,217,420 | 8/1980 | Langejan | 426/62 |
| 4,226,940 | 10/1980 | Storrs | 435/260 |
| 4,232,045 | 11/1980 | Pomper et al. | 426/62 |
| 4,341,871 | 7/1982 | Langejan et al. | 435/256 |
| 4,405,650 | 9/1983 | Spadafora | 435/256 |
| 4,719,114 | 1/1988 | Percel | 426/62 |
| 4,863,865 | 9/1989 | Franks | 435/256 |

FOREIGN PATENT DOCUMENTS

| 0259739 | 3/1988 | European Pat. Off. . |
| 1530866 | 3/1977 | Germany . |

OTHER PUBLICATIONS

Mikata et al, Inst. Ferment. Res. Commun (Osaka), O (13), 1987, pp. 59–68 (Biosis Abstract).
Jermini et al, J. Food Prot., 50(5), 1987, pp. 414–417 (Biosis Abstract).
Sidyakina et al, Prikl. Biokhim. Mikrobiol., 22 (6), 1986, pp. 840–843 (Biosis Abstract).
H. C. Bold (1967) *Morphology of Plants*, Second Edition, Harper & Row, NY, pp. 7 and 142.
Oura et al (1980) *VIth International Fermentation Symposium and Vth International Symposium on Yeasts*, London, Ontario, Canada Abstract Y-1.3.4(L), p. 213.

*Primary Examiner*—Marian C. Knode
*Assistant Examiner*—Susan M. Dadio
*Attorney, Agent, or Firm*—Birch, Stewart, Kolasch & Birch

[57] ABSTRACT

A novel high density liquid or paste yeast preparation, which comprises approximately 1–20% (w/w) of a polyol selected from propylene glycol, glycerol, non-fermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof, and fresh yeast. The high density yeast preparation has a density of more than 800 g yeast (of dry matter 27–29 %) per liter of preparation, and the concentration of the polyol in the extracellular liquid is 5–50 % (w/v). The preparation has an improved capacity for retaining its activity, dissolving instantly, and for being easily batched. It is uniformily suspendable and tolerant of repeated freezing and thawing. The liquid high density yeast preparation has a viscosity of less than 200 centiPoise (cP) at 20° C. Methods for producing the high density yeast preparation, as well as for the preparation of improved quality baker's, brewer's, distiller's and wine yeast are disclosed.

21 Claims, 5 Drawing Sheets

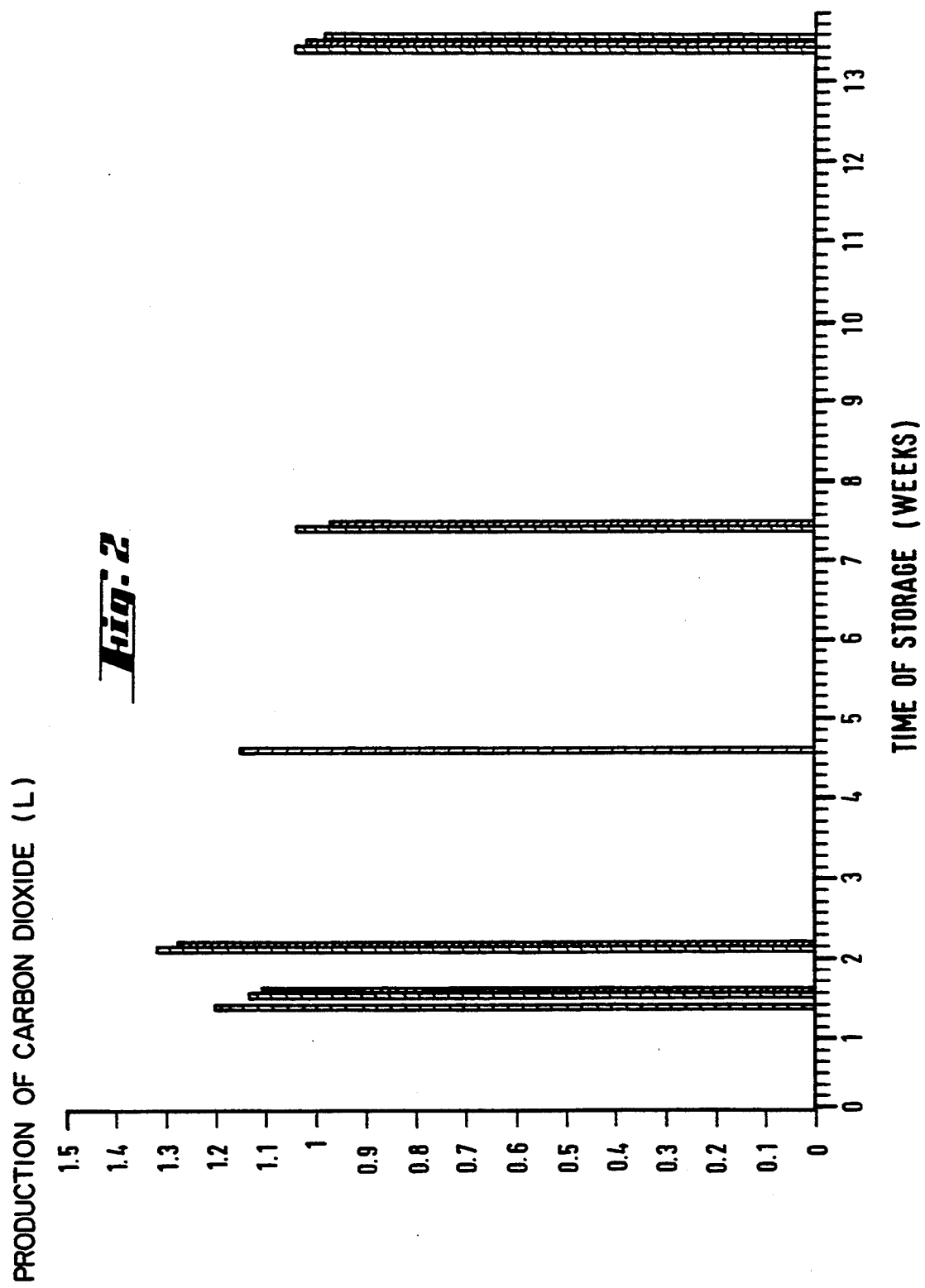

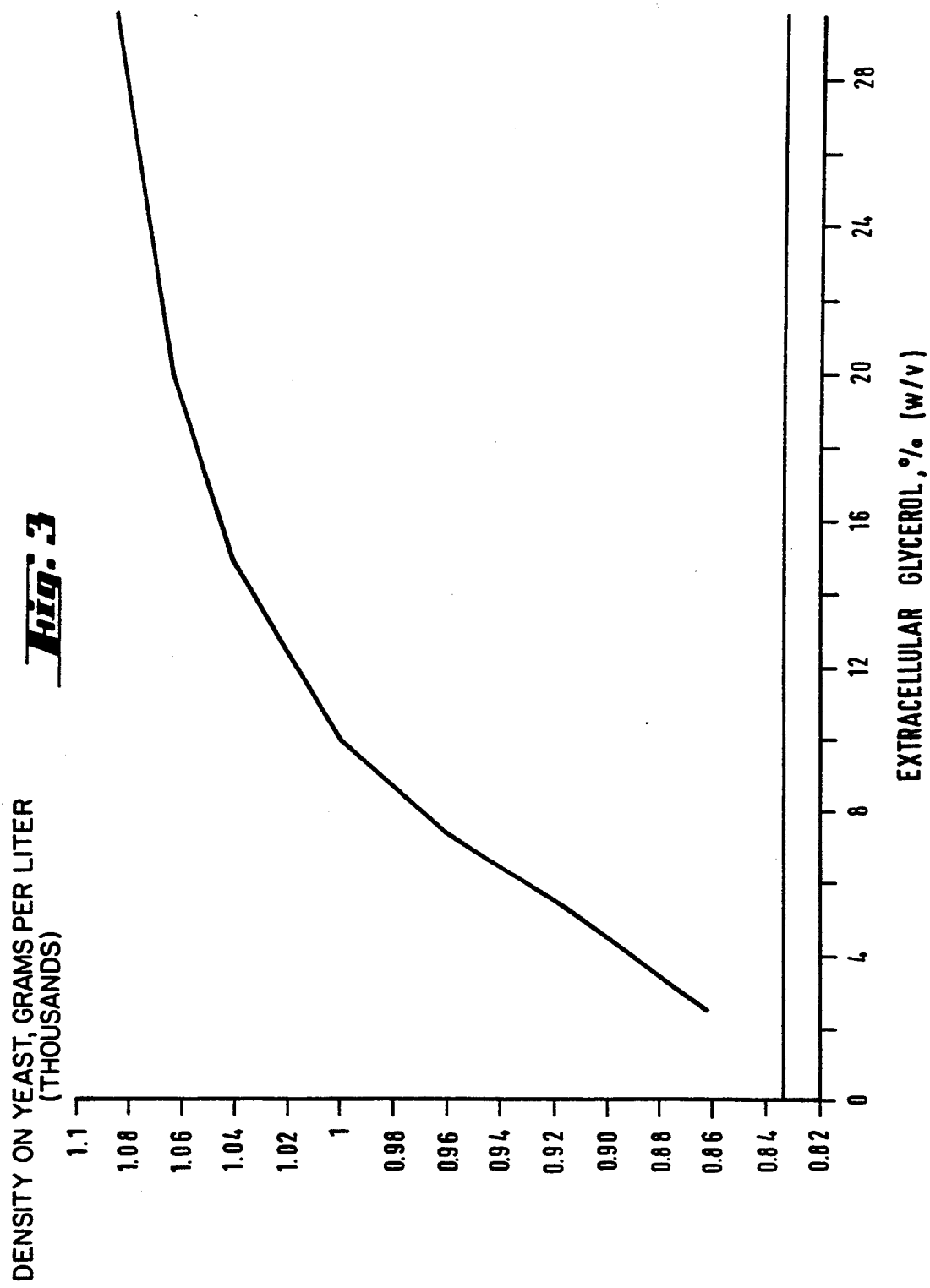

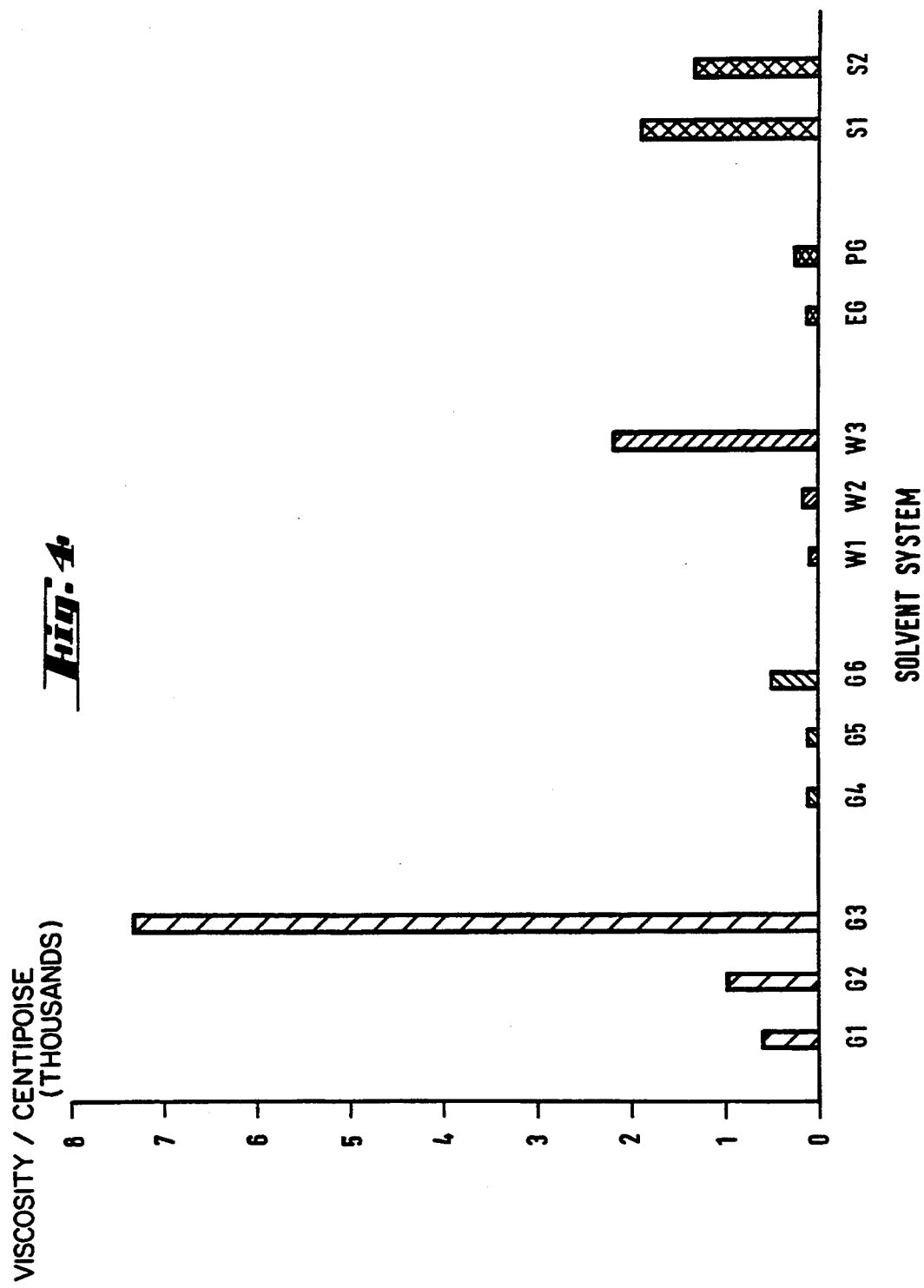

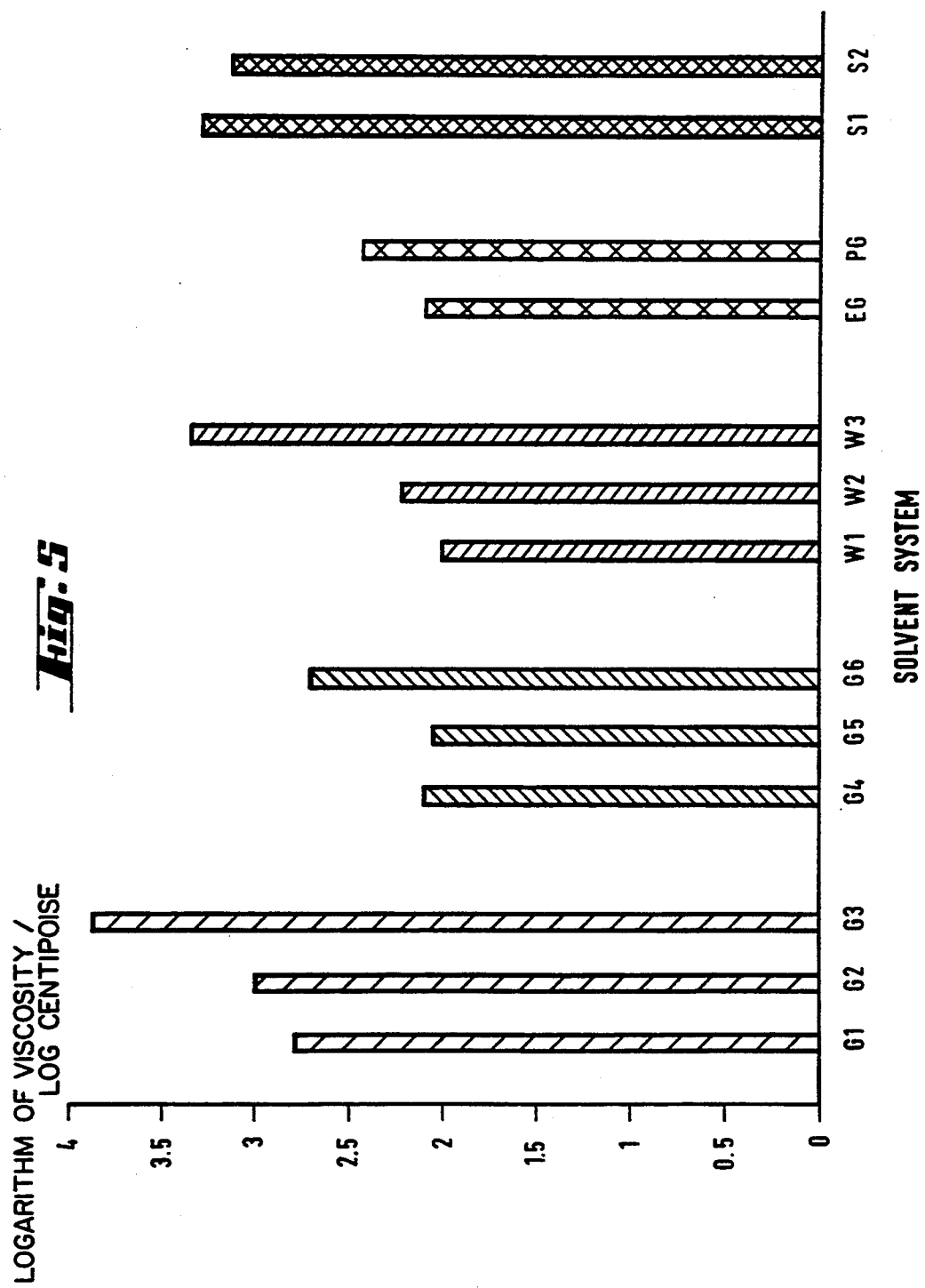

HIGH DENSITY YEAST PREPARATION, A METHOD FOR PRODUCING IT AND THE USE OF THE PREPARATION

This application is a continuation of application Ser. No. 07/655,816 filed on Feb. 15, 1991, now abandoned.

BACKGROUND OF THE INVENTION

1. Technical field

The present invention is related to a novel high density liquid or paste yeast preparation containing polyolic compounds, preferably nontoxic polyolic compounds such as glycerol, and also to a method for producing the preparation, as well as using the same.

2. Description of Related Art

At present, baker's yeast is usually supplied for households in the form of fresh compressed yeast in packages or in powder form as active dry yeast. Small and medium sized bakeries receive their yeast in fresh form, or use dry yeast. A so called "cream yeast" or "yeast milk", i.e., a water solution of fresh yeast, in which the proportion of yeast (of dry matter 27–29%) is approximately 750 grams per liter of product, is supplied to the largest bakeries. The "cream yeast" or "liquid yeast" is prepared by separators, and the maximum yeast content of the product is determined by the separating effect of the separator used.

None of the said forms in which yeast is supplied is fully satisfactory. The time elapsing from delivery to sale and use is often too long. In households, the need for yeast cannot be planned in advance, and therefore fresh yeast may not be available. Cake stored in the refrigerator may have dried or become moldy or inactive. Dry yeast remains, in principle, active for long periods but in any case must be dissolved and "awakened" properly to recover full activity.

As noted above, small and medium-sized bakeries use dry yeast. With respect to the use of fresh compressed yeast, problems include assessment of the necessary stock, and the batching and crumbling of the yeast, which is difficult using automatic equipment.

Because yeast cells are denser than water, the "cream yeast" supplied for the larger bakeries has a tendency to sediment at the bottom of the container in which it is transported. Consequently, the yeast cream has to be stirred before use. Finally, one cubic meter contains more than 200 liters of excess water.

The batching and storage of yeast for baking is not completely without problems, either for a home baker or for a professional baker.

SUMMARY OF THE INVENTION

Thus, the object of the present invention includes eliminating the disadvantages described above.

An object of the present invention is to provide a new, easily batched, high density liquid or paste yeast preparation.

Another object of the present invention is to provide a yeast preparation which is easily suspended via the use of a polyolic compound, preferably glycerol, which acts as a carrier for the yeast cells.

Glycerol is an especially advantageous additive for the production of a yeast preparation because it is an approved food additive which can be used, e.g., as a stabilizer in coffee-bread.

Another object of the present invention is to provide a liquid yeast preparation, the density of which can be regulated to produce preparations of desired yeast density. This property is due to the fact that the addition of the polyolic compound, preferably glycerol, produces the unexpected result of allowing the preparation of a high density yeast product, the density of which is much higher than the density of conventional liquid yeast ("cream yeast") preparations.

Yet another object of the present invention is to provide a yeast preparation which has an improved capacity for tolerating freezing temperatures, and which can thus tolerate repeated thawing and refreezing.

Yet a further object of the present invention is to provide a liquid yeast preparation which does not sediment, and thus does not require stirring before use. Said liquid yeast can be used as a substitute for the conventional cream yeast. In this form, a one cubic meter container can carry one ton of high density liquid yeast instead of 750 to 800 kilograms of conventional liquid yeast.

The present invention is related to a novel, high density liquid or paste yeast preparation and its production. The preparation contains polyolic compounds, preferably nontoxic polyolic compounds, such as propylene glycol, glycerol, nonfermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof. In a preferred embodiment of the invention, the preparation contains 10–200 g of glycerol per kg of fresh compressed yeast (of dry matter 27–29%). The concentration of the polyolic compound in the extracellular liquid is 5–50% (w/v).

The preparation is characterized by the fact that it contains more than 800 g yeast (of dry matter of 27–29%) per liter of liquid or paste. The paste form of the preparation according to the present invention may contain up to 1100 g yeast per liter of preparation. The corresponding liquid preparation typically contains 800 to 1050 g yeast per liter, and is further characterized by the low viscosity of the liquid, typically less than 200 cP (20° C.).

The preparation of the novel high density yeast product, and its use, are also disclosed. The preparation is useful, for example, as a substitute for "cream yeast," and improves upon the properties of both "conventional" baker's yeast and baker's special yeasts such as sourdough yeast, brewer's yeast, distiller's yeast, and wine yeasts. The novel, high density, liquid or paste yeast preparations are easy to batch, and dissolve instantly.

BRIEF DESCRIPTION OF DRAWINGS

FIG. 2 depicts the retention of activity by a glycerol yeast preparation which has been frozen once.

FIG. 3 depicts the liquefication of yeast with glycerol.

FIG. 4 depicts the effect of different polyols on yeast, expressed as the viscosity of the liquid yeast produced.

FIG. 5 depicts the effect of different polyols on yeast, expressed as the logarithm of the viscosity of the liquid yeast produced.

DETAILED DESCRIPTION OF THE INVENTION

Figure 1:
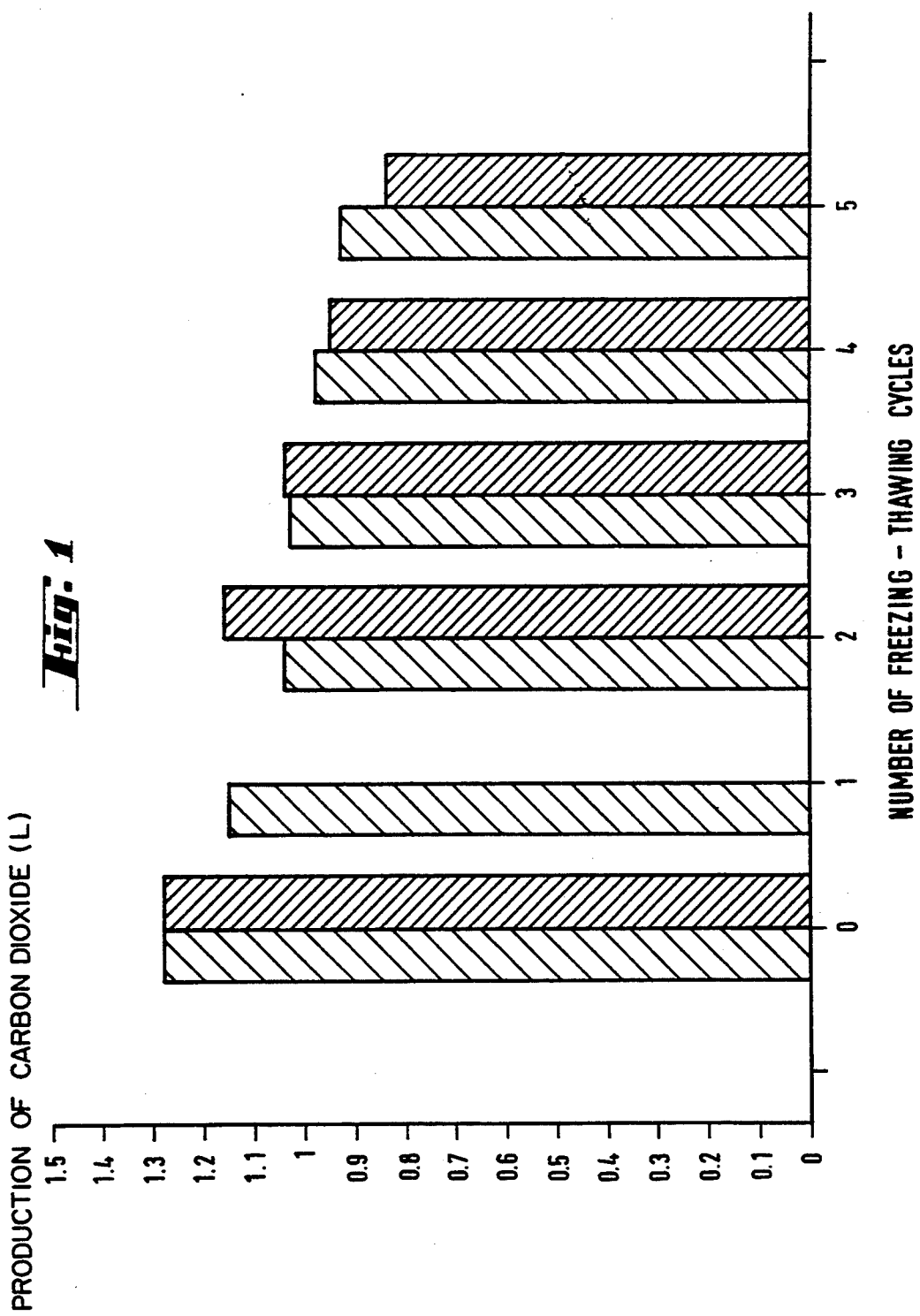
FIG. 1 depicts the effect of freeze-thawing cycles on the activity of a glycerol yeast preparation.

The present invention is based on the quite unexpected observation that an extremely small amount of a polyolic compound, preferably glycerol, makes the compressed yeast melt or become liquefied. In FIG. 3, the liquefication of yeast in glycerol is shown. It was also found that the volume of the mixture of compressed yeast and glycerol or other polyol taken together may be even smaller than the volume of the yeast before addition of the polyol. These unexpected observations are industrially applicable because they make it possible to standardize, dilute, or concentrate the yeast preparation according to the present invention such that its density corresponds to the amount of yeast in the preparation substituted by the new product.

The form of the product is a function of both the yeast content and the extracellular concentration of the polyol. The curve in FIG. 3 indicates the approximate borderline of these forms: the area above the curve indicates the range where the product tends to be a paste; within the area below the curve, the product is readily flowing. The horizontal line at 830 grams per liter shows the maximum efficacy of the conventional separator technology for yeast-water solutions.

The invention is based on the following commonly known facts. Polyolic compounds, such as glycol and glycerol, prevent freezing, and in the event of freezing, protect proteins from denaturation. Polyolic compounds are also used as auxiliary agents in the laboratory for storing bacteria and yeasts (Minicool process, −70° C.). The storage and stabilization of bacteria and yeast strains with glycerol are known methods (U.S. Pat. No. 4,226,940; U.S. Pat. No. 3,960,664; U.S. Ser. No. Re 28,276; EP 259 739; and GB 1 530 866).

The yeast solvating property of polyolic compounds, preferably glycerol, has not been previously disclosed or applied industrially.

This phenomenon is based on the fact t hat commercial yeast contains approximately 72% water, of which 70% is intracellular, and the rest extracellular (Oura, E. & Tanner, R., Changes in the Content of External and Internal Water in Pressed Yeast during Storage, Int. Ferment. Symp. Yeasts, 5th, London, Ont., Canada 1980, Abstracts, p 213). Thus, approximately 20% of the fresh weight of yeast is extracellular water and, for example, glycerol must be added to yeast at the rate of 10% by weight so that the extracellular liquid would be 30% in proportion to glycerol, as shown in Table 1. Even lower concentrations will suffice to meet the functions of the yeast preparation described in the present invention.

TABLE 1

Amount of glycerol to be added to compressed yeast (of dry matter 27-29%) in proportion to the extracellular glycerol content.

| Glycerol addition g/100 g | Extracellular glycerol % |
|---|---|
| 10.00 | 31.6 |
| 9.25 | 30.6 |
| 5.40 | 20.0 |
| 3.80 | 15.0 |
| 2.40 | 10.0 |
| 1.13 | 5.0 |

By using polyolic compounds, preferably glycerol, the density of the extracellular liquid can be adjusted to correspond to the density of the yeast cells, whereby the sedimentation typical of conventional watery "cream yeast" prepared by separators is avoided.

The viscosity of the high density liquid or paste yeast preparation according to the present invention is low, and so a suspension corresponding in its yeast content, i.e., cells per liter, to compressed yeast can be poured and pumped like a liquid. The viscosity of a high density liquid yeast preparation is typically less than 200 centiPoise (cP) at 20° C. The viscosities at 20° C. of conventional liquid yeasts and of different yeast preparations according to the present invention are shown in more detail in FIG. 4.

Bars G1, G2 and G3 indicate the viscosities of high density yeasts that contain 1040 grams of yeast (of dry matter of 27-29%) per liter, the extracellular concentrations of glycerol being 14.1, 10.6 and 7.0 percent (w/v), respectively.

Bars G4, G5 and G6 indicate the viscosities of high density yeasts that have been adjusted to contain 1000 grams yeast (of dry matter of 27-29%) per liter, the extracellular concentrations of glycerol being 14.9, 11.1 and 7.4% (w/v), respectively.

Bars W1, W2 and W3 indicate the viscosities of conventional yeast creams in water with yeast contents of 750, 800 and 830 grams per liter, respectively.

Bars EG and PG indicate the viscosities of high density yeast preparations that contain 1040 grams of yeast per liter, the extracellular concentrations of ethylene glycol and propylene glycol being 17.8 and 16.6% (w/v), respectively.

Bars S1 and S2 indicate the viscosities of high density yeast preparations that contain 1000 and 960 grams yeast and extracellular concentrations of sorbitol of 8.3 and 10.9% (w/v), respectively.

FIG. 5 shows the logarithms of the viscosities of the yeast preparations mentioned above.

The high density yeast preparation according to the present invention comprises 1-20% (w/w) of a polyolic compound selected from the group consisting of propylene glycol, glycerol, non-fermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof, and 80-99% (w/w) fresh yeast (of dry matter 27-29%).

Glycerol is the preferred polyol of the present invention. It is typically used as 1-99.5%, preferably as 60 to 90% (w/v) solutions.

Xylose, sorbitol, and other solid polyolic compounds are suitable, but are not as convenient as glycerol because they must be dissolved before use. They are typically used as 20-80% (w/v) solutions. In some preferred embodiments of the present invention, 10-100 ml of 30-100% glycerol per 1 kg of fresh yeast; 60-90 ml of 30-70% (w/v) xylose per 1 kg of fresh yeast; 60-120 ml of 30–50% (w/v) sorbitol per 1 kg of fresh yeast; and 100–250 ml of 30–50% (w/v) soluble starch per 1 kg of fresh yeast are used.

Soluble polysaccharides such as Zulkowsky's starch are useful, but may cause minor problems because they may contain fermentable sugars, which make the yeast foam during preparation. However, when the fermentable sugars have been spent, the soluble starch yeast preparation can be used in the same way as the other preparations containing polyolic compounds.

The high density yeast preparation according to the present invention is a liquid or a paste, and in a preferred embodiment, contains 10–200 g glycerol per kg of fresh compressed yeast. The glycerol concentration in the extracellular liquid is 5–50%. The preparation tolerates freezing temperatures and repeated freezing, thawing and refreezing. The liquid high density preparation has a low viscosity, i.e., less than 200 centiPoise (cP) at 20° C., because the aggregation of yeast cells in it is inhibited. Thus, the preparation is easy to batch, and dissolves instantly. The density of the extracellular liquid of the yeast cells in the preparation approaches the density of the yeast cells, in which case the sedimentation of the yeast cells is reduced, and the preparation is advantageous for many industrial purposes.

The high density yeast preparation is characterized by having a density of more than 800 g yeast per liter yeast preparation, the concentration of the polyolic compound, preferably glycerol, in the extracellular liquid being 5–50% (w/v).

This preparation has the capability of retaining its activity, dissolving instantly, and being easily batched. It is uniformily suspendable, and tolerant of repeated freezing and thawing.

In its liquid form, the high density yeast preparation contains 3–20% (w/w) of a polyolic compound selected from the group consisting of propylene glycol, glycerol, non-fermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof, and 80–97% (w/w) fresh yeast. In the preferred embodiment, it contains 30–200 g glycerol per kg fresh compressed yeast. Said high density liquid yeast preparation has a typical yeast content of 830–1050 g yeast (of dry matter 27–29%) per liter of preparation, the concentration of the polyolic compound in the extracellular liquid being 10–50, preferably 20% (w/v). This preparation typically has a viscosity of less than 200 centiPoise (cP) at 20° C.

In its paste form, the high density yeast preparation contains about 1–4% (w/w) of a polyolic compound selected from the group consisting of propylene glycol, glycerol, non-fermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof, and about 96–99% (w/w) fresh compressed yeast. In the preferred embodiment, it contains 10–40 g glycerol per kg fresh compressed yeast. Said paste high density yeast preparation normally has a yeast content of more than 800 grams of yeast (of dry matter 27–29%) per liter yeast preparation, the concentration of the polyolic compound in the extracellular liquid being 5–15, preferably 10% (w/v).

Shifting to the use of the yeast preparation according to the present invention will not cause batching problems for the user, since the yeast preparation can easily be adjusted so that 1 ml of the yeast preparation corresponds to 1 g of fresh yeast.

The high density liquid or paste yeast preparation according to the present invention is prepared by adding 1–20% (w/w) of a polyolic compound selected from the group consisting of propylene glycol, glycerol, non-fermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof, to fresh yeast by the aid of continuous, gentle agitation. In the preferred embodiment of the present invention, 10–200 g of glycerol are added to one kilogram of yeast cake. When the concentration of the polyolic compound, preferably glycerol, increases, the viscosity of the yeast suspension decreases sharply, i.e., the yeast becomes fluid, liquid-like.

This phenomenon is assumed to be due to the adherence of the polyolic compounds, preferably glycerol, to the glycan components of the glycoproteins of the exterior wall of the yeast, and to their prevention, more effectively than water, of the formation of aggregates of yeast. Since the particle size of the "unicellular" yeast thus formed is small, and because the lubricating effect of the polyol makes the friction between the cells low, the solution flows readily.

If a high density liquid yeast preparation is desired, 3–20% (w/w) of a polyolic compound selected from the group consisting of propylene glycol, glycerol, non-fermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof, are added to fresh compressed yeast with the aid of gentle agitation. In a preferred embodiment of the invention, 30–200 g glycerol per kg fresh yeast are added with the aid of gentle agitation.

If a high density paste yeast preparation is desired, 1–4% (w/w) of a polyol selected from the group consisting of propylene glycol, glycerol, non-fermentable mono- or oligosaccharides or sugar alcohols such as xylose, mannitol and sorbitol, soluble oligo- or polymeric carbohydrates such as partially hydrolysed starch, cellulose, agarose, or polyethylene glycol, or mixtures thereof, is added to the fresh compressed yeast with the aid of continuous gentle agitation. In the preferred embodiment of the invention, 10–40 g glycerol per kg fresh yeast is added.

The high density liquid yeast preparation is used as a substitute for cream yeast, and is packaged in large containers for large bakeries.

The high density liquid yeast preparation is distributed either in a single consumer package containing more than one portion, optionally provided with a measuring device such as an automatic batcher, or in a packaged combination comprising a number of single portion containers.

The high density paste yeast preparation is preferably used in extrudable form, such as in tubes, squeezable capsules, or metal foil or plastic bags, each containing one portion per package. Alternatively, the preparation can be packed in small containers, in the same manner as margarine.

In addition, the present invention is advantageous for the preparation of baker's special high density yeasts such as sourdough yeast with improved quality, and for the preparation of improved high density brewer's yeast and wine yeasts as well.

The yeast preparation according to the present invention is characterized in that in both of its forms, it can be mixed with the dough without being premixed or "awakened".

The yeast preparation according to the present invention can be stored at freezing temperatures better than yeast preparations containing no polyolic compound additive. Thawing of the yeast preparation is also easier due to the lower energy, only about 50 percent, needed for the solid to liquid phase transition as compared with that required for the thawing of a conventional frozen liquid yeast.

In addition, the yeast preparation according to the present invention can be thawed and frozen several times without significant loss of activity.

The yeast according to the present invention in its frozen form is suitable for use not only in households, but also in small and medium-sized bakeries.

Owing to its even, liquid-like consistency, it mixes easily and can be batched with automatic equipment. Frozen storage will ensure that the quality remains stable. When the yeast is stored in an airtight container and frozen, drying as well as mold and bacterial contamination and growth are avoided.

The embodiments of the present invention are described in more detail in the following Examples.

EXAMPLE 1

Preparation of a high density liquid yeast with glycerol

A 30% (w/v) preparation which flows very well is prepared by suspending 1 kg of fresh yeast in 94 g of 99.5% glycerol of USP (US Pharmacopea) quality by adding the yeast in small batches while constantly stirring the suspension gently. The preparation is suitable for both a batch package, and for packages which can be used several times, with thawing before use and freezing afterwards.

The preparation is characterized by a glycerol concentration of 10–50% in the extracellular liquid.

EXAMPLE 2

Preparation of a high density paste yeast with glycerol

A preparation with a concentration of 10% (w/v) is prepared by suspending 1 kg of fresh yeast in 25 g of 99.5% glycerol of USP quality by adding the yeast in small batches while constantly stirring the suspension gently. The preparation is suitable for batch packaging. The preparation is characterized by a glycerol concentration of 5–15% in the extracellular liquid.

EXAMPLE 3

Retaining the activity of the yeast preparation while frozen

The yeast preparation prepared in Example 2 was frozen in batches of 5 g, which were stored at $-20°$ C. for 1–13 weeks. The batch to be investigated was dissolved in water at 30° C., and its activity was measured by using as an indicator a standardized baking experiment in which 280 g of wheat flour, 170 ml of water, 4.0 g of table salt and 5.0 ml of the yeast preparation (corresponding to 5.0 g of fresh yeast) were used for the dough. The dough was allowed to raise in an SJA (S. J. A., Stockholm, Sweden) fermentograph at 35° C. under standardized conditions. The dough was allowed to rise for one hour, whereafter it was patted down and allowed to rise once more for one hour. The production of carbon dioxide per 2 h was measured. The results are shown in FIG. 2 for parallel samples (1) and (2).

EXAMPLE 4

Effect of thawing-freezing cycles on the activity of the yeast preparation

The effect of repeated thawings and freezings on the yeast prepared in Example 2 was investigated during five cycles, the duration of each cycle being 1 week. The preparation was allowed to thaw at room temperature or in 30° C. water before measuring the activity, and was thereafter placed in the freezer ($-20°$ C.) for one week. The activity was measured by using as an indicator the baking experiment described in Example 3. The results are shown in FIG. 1 for two parallel samples (1) and (2).

EXAMPLE 5

Application to brewer's yeast

Each of the preparations described in Examples 1, 2 and 5 can be applied to a typical brewer's yeast, e.g., *Saccharomyces uvarum* or *S. carlsbergensis*. The typical user of such a preparation is a brewery which does not itself wish to produce the yeast it needs. The brewery can, of course, itself produce its yeast by the method according to the present invention. It is advantageous to use the method or preparation according to the present invention if the brewery is small and the yeast is needed infrequently. A product of uniform quality can be obtained by using the method and preparation according to the present invention.

EXAMPLE 6

Application to sourdough yeast

Sourdough yeast is a traditional mixture that consists of a suitable yeast, e.g., *Saccharomyces cerevisiae* or *Candida milleri*, and suitable bacteria of the genus Lactobacillus. There are hardly any such commercial products available. Bakers traditionally use their own sourdoughs for many generations. In such case, the cessation of activity of the sourdough is the limiting factor. By the method according to the present invention, it is also possible to produce, in a highly controlled manner, a mixed suspension of yeast and suitable bacteria, the properties of the suspension being stable even during long time storage in bakeries, and the suspension being capable of being offered for retail sale in the manner described in Examples 1 and 2.

EXAMPLE 7

Application to wine yeast

Wine yeasts are usually delivered to consumers as active dry yeast powders. The comments above with respect to breweries apply to wineries as well. A good preparation can be cultivated and compressed in the ordinary manner, and then dissolved in a suitable form as described in Examples 1, 2, 8 and 9.

EXAMPLE 8

Preparation of a xylose high density yeast

A high density liquid yeast preparation with xylose was made by dissolving 1 kg of fresh yeast (of dry matter 27–29%) in 90 milliliters of a 70% (w/v) water solution of xylose, and mixing gently to give a homogeneous suspension. The yeast content of the product was 1000 grams per liter, and the extracellular concentration of xylose was 23% (w/v).

EXAMPLE 9

Preparation of a high density yeast with sorbitol

High density liquid or paste yeast preparations with sorbitol were made by dissolving 1 kg of fresh yeast (of dry matter 27-29%) in either 80 ml or 120 ml of 30% (w/v) sorbitol, and mixing gently. The extracellular sorbitol concentrations were then 8.3 or 10.9% (w/v), and the corresponding yeast contents 1000 and 960 grams per liter, respectively.

EXAMPLE 10

High density liquid yeast preparation with soluble starch

A high density liquid yeast preparation with soluble starch was made by dissolving 1 kg of fresh yeast (of dry matter 27-29%) in 240 ml of a 30% water solution of partially hydrolysed starch.

EXAMPLE 11

The viscosity of high density liquid yeast preparations

The viscosity of a high density liquid yeast preparation is typically less than 200 centiPoise (cP) at 20° C. The viscosities at 20° C. of conventional liquid yeast preparations and of different yeast preparations according to the present invention are shown in detail in FIGS. 4 and 5.

Bars G1, G2 and G3 indicate the viscosities at 20° C. of high density yeasts that contain 1040 grams yeast (of dry matter of 27-29%) per liter, the extracellular concentrations of glycerol being 14.1, 10.6 and 7.0 percent (w/v), respectively.

Bars G4, G5 and G6 indicate the viscosities of high density yeasts that have been adjusted to contain 1000 grams yeast (of dry matter of 27-29%) per liter the extracellular concentrations of glycerol being 14.9, 11.1 and 7.4 % (w/v), respectively.

Bars W1, W2 and W3 indicate the viscosities of conventional yeast creams in water with yeast contents of 750, 800 and 830 grams per liter, respectively.

Bars EG and PG indicate the viscosities of high density yeasts that contain 1040 grams of yeast per liter, the extracellular concentrations of ethylene glycol and propylene glycol being 17.8 and 16.6% (w/v), respectively.

Bars S1 and S2 indicate the viscosities of high density yeasts that contain 1000 and 960 grams yeast, the extracellular concentrations of sorbitol being 8.3 and 10.9% (w/v), respectively.

I claim:

1. A high density yeast preparation, comprising:
   1-20% by weight of glycerol per total weight of said glycerol and fresh compressed yeast; and
   80-99% by weight of fresh compressed yeast per total weight of said glycerol and fresh compressed yeast, said high density yeast preparation having a density of more than 800 grams of yeast per liter yeast preparation, said yeast having a dry matter content of 27-29%, the concentration of said glycerol in extracellular liquid of said fresh yeast being 5-50%, w/v, said preparation having the capability of retaining its activity, of dissolving instantly, and of being easily batched, and which is uniformly suspendable and tolerant repeated freezing and thawing, wherein said yeast is selected from the group consisting of brewer's yeast sourdough yeast, wine yeast, baker's yeast, and distiller'3 s yeast.

2. The high density yeast preparation of claim 1, wherein said high density yeast preparation comprises 10-200 grams of glycerol per kilogram of fresh yeast and has a density of more than 800 grams of yeast per liter of preparation, said yeast having a dry matter content of 27-29%, and wherein the glycerol concentration in the extracellular liquid is 5-50%, w/v.

3. The high density yeast preparation of claim 1, which is in the form of a frozen liquid preparation.

4. The high density yeast preparation of claim 1, which is in the form of a liquid preparation.

5. The high density yeast preparation of claim 1 which is in the form of a paste.

6. A high density liquid yeast preparation, comprising:
   3-20% by weight of glycerol per total weight of said glycerol and fresh yeast; and
   80-97% by weight of fresh compressed yeast per total weight of said glycerol and fresh yeast, said high density liquid yeast preparation having a density of more than 800 grams of yeast per liter of preparation, said yeast having a dry matter content of 27-29%, the concentration of said glycerol in extracellular liquid of said fresh yeast being 10-50%, w/v, a viscosity of less than 200 centiPoise at 20° C., having the capability of retaining its activity, of dissolving instantly, and of being easily batched, and which is uniformly suspendable and tolerant of repeated freezing and thawing, wherein said yeast is selected from the group consisting of brewer's yeast, sourdough yeast, wine yeast, baker's yeast, and distiller's yeast.

7. The high density liquid yeast preparation of claim 6, wherein said yeast preparation comprises 30-200 grams of glycerol per kilogram fresh yeast, has a density of more than 800 grams of yeast per liter of preparation, said yeast having a dry matter content of 27-29%, and a glycerol concentration in said extracellular liquid of 10-50%, w/v, and wherein said yeast preparation has a viscosity of less than 200 centiPoise at 20° C.

8. A high density paste yeast preparation, comprising:
   1-4% by weight of glycerol per total weight of said glycerol and fresh yeast; and
   96-99% by weight of fresh compressed yeast per total weight of said glycerol and fresh yeast, said high density paste yeast preparation having a density of more than 800 grams of yeast per liter of preparation, said yeast having a dry matter content of 27-29%, a concentration of said glycerol in extracellular liquid of 5-15%, w/v, the capability of retaining its activity, of dissolving instantly, and of being easily batched, and which is uniformly suspendable and tolerant of repeated freezing and thawing, wherein said yeast is selected from the group consisting of brewer's yeast, sourdough yeast, wine yeast, baker's yeast, and distiller's yeast.

9. The high density paste yeast preparation of claim 8, wherein said yeast preparation comprises 10-40 grams of glycerol per kilogram fresh yeast, has a density of more than 800 grams of yeast per liter of preparation, said yeast having a dry matter content of 27-29%, and wherein the glycerol concentration in the extracellular liquid is 5-15%, w/v.

10. A method for preparing a high density yeast preparation, comprising:

adding, with the aid of gentle agitation, (a) 1–20% by weight of glycerol per total weight of said glycerol and fresh compressed yeast; and (b) 80–99% by weight of fresh compressed yeast per total weight of said glycerol and fresh compressed yeast, said high density yeast preparation having a density of more than 800 grams of yeast per liter yeast preparation, said yeast having a dry matter content of 27–29%, the concentration of said glycerol in extracellular liquid of said fresh yeast being 5–50%, w/v, said preparation having the capability of retaining its activity, of dissolving instantly, and of being easily batched, and which is uniformly suspendable and tolerant of repeated freezing and thawing, wherein said yeast is selected from the group consisting of brewer's yeast, sourdough yeast, wine yeast, baker's yeast, and distiller's yeast.

11. The method of claim 10, wherein 10–200 grams of glycerol per kilogram of fresh yeast are added to said fresh compressed yeast with the aid of gentle agitation.

12. A method for preparing a high density liquid yeast preparation, comprising:

adding, with the aid of gentle agitation, (a) 3–20% by weight of glycerol per total weight of said glycerol and fresh compressed yeast; and (b) 80–97% by weight of fresh compressed yeast per total weight of said glycerol and flesh compressed yeast, said high density liquid yeast preparation having a density of more than 800 grams of yeast per liter of preparation, said yeast having a dry matter content of 27–29%, the concentration of said glycerol in extracellular liquid of said fresh yeast being 10–50%, w/v, a viscosity of less than 200 centiPoise at 20° C., having the capability of retaining its activity, of dissolving instantly, and of being easily batched, and which is uniformly suspendable and tolerant of repeated freezing and thawing, wherein said yeast is selected from the group consisting of brewer's yeast, sourdough yeast, wine yeast, baker's yeast, and distiller's yeast.

13. The method of claim 12, wherein 30–200 grams of glycerol per kilogram of fresh compressed yeast are added to said fresh compressed yeast with the aid of gentle agitation.

14. A method for preparing a high density paste yeast preparation, comprising:

adding, with the aid of gentle agitation, (a) 1–4% by weight of glycerol per total weight of said glycerol and fresh compressed yeast; and (b) 96–99% by weight of fresh compressed yeast per total weight of said glycerol and fresh compressed yeast, said high density paste yeast preparation having a density of more than 800 grams of yeast per liter of preparation, said yeast having a dry matter content of 27–29%, a concentration of said glycerol in extracellular liquid of 5–15%, w/v, the capability of retaining its activity, of dissolving instantly, and of being easily batched, and which is uniformly suspendable and tolerant of repeated freezing and thawing, wherein said yeast is selected from the group consisting of brewer's yeast, sourdough yeast, wine yeast, baker's yeast, and distiller's yeast.

15. The method of claim 14, wherein 10–40 grams of glycerol per kilogram of fresh compressed yeast are added to said fresh compressed yeast with the aid of gentle agitation.

16. The method of claim 10, 11, 12 or 13, wherein said glycerol is added to fresh compressed yeast.

17. The high density sourdough yeast preparation prepared by the method of claim 10.

18. The high density brewer's yeast preparation prepared by the method of claim 10.

19. The high density baker's yeast preparation prepared by the method of claim 10.

20. The high density wine yeast preparation prepared by the method of claim 10.

21. The high density distiller's yeast preparation prepared by the method of claim 10.

* * * * *